United States Patent [19]

McCullough et al.

[11] Patent Number: 5,167,753

[45] Date of Patent: Dec. 1, 1992

[54] APPARATUS FOR MAKING BEADED DENTAL FLOSS OR THE LIKE

[76] Inventors: Edward E. McCullough; Kevin W. McGaha, both of Box 46, Brigham City, Utah 84302

[21] Appl. No.: 598,838

[22] Filed: Oct. 15, 1990

[51] Int. Cl.⁵ .......................................... B32B 31/00
[52] U.S. Cl. .................................. 156/518; 156/514; 156/519; 156/257; 132/323; 132/327; 425/289
[58] Field of Search ............... 156/510, 257, 513, 514, 156/517, 518, 519, 516; 132/323, 327; 425/289

[56] References Cited

U.S. PATENT DOCUMENTS

| | | | |
|---|---|---|---|
| 1,815,408 | 7/1931 | Jordan | 132/323 |
| 3,631,869 | 1/1972 | Espinosa | 132/323 |
| 3,780,608 | 1/1972 | Brown | 156/514 |
| 3,843,297 | 10/1974 | Espinosa | 425/289 |
| 3,974,842 | 8/1976 | Chodorow | 132/323 |
| 4,006,750 | 2/1977 | Chodorow | 132/323 |
| 4,753,254 | 6/1988 | McCullough et al. | 132/323 |
| 4,776,357 | 10/1988 | McCullough et al. | 132/327 |
| 4,898,196 | 2/1990 | Eason | 132/327 |

*Primary Examiner*—Mary Lynn Theisen
*Assistant Examiner*—David Reifsnyder
*Attorney, Agent, or Firm*—Edward E. McCullough

[57] ABSTRACT

A filament of thermoplastic material is formed into a continuous strand of connected beads having a longitudinal slit that penetrates about half way into each bead. This is done by passing the filament between a pair of rotating mold wheels having matching, hemispherical cavities in their outer edges with a central, circumferential flange in the edge of one wheel-the flange forming the slit. An end bead of the filament is loaded into a first clamp that feeds it to second clamp that grasps the bead while a knife severs it from the strand. The second clamp is then moved to force its held bead onto a short span of floss being held by a third clamp, so that the floss is press-fitted into the slit in the bead. The bead and floss are then released by their respective clamps, and a fourth clamp grasps the floss and moves it forward for the required distance between beads so that the next bead can be pressed thereon. Each pressed-on bead is then permanently fixed to the floss with a tiny drop of glue from a dispenser and passed through a heated drying tube. The beaded floss is then stored on a reel. The devices described are operated by a series of eight solenoids, the operations of which are timed by an electromechanical timer.

32 Claims, 2 Drawing Sheets

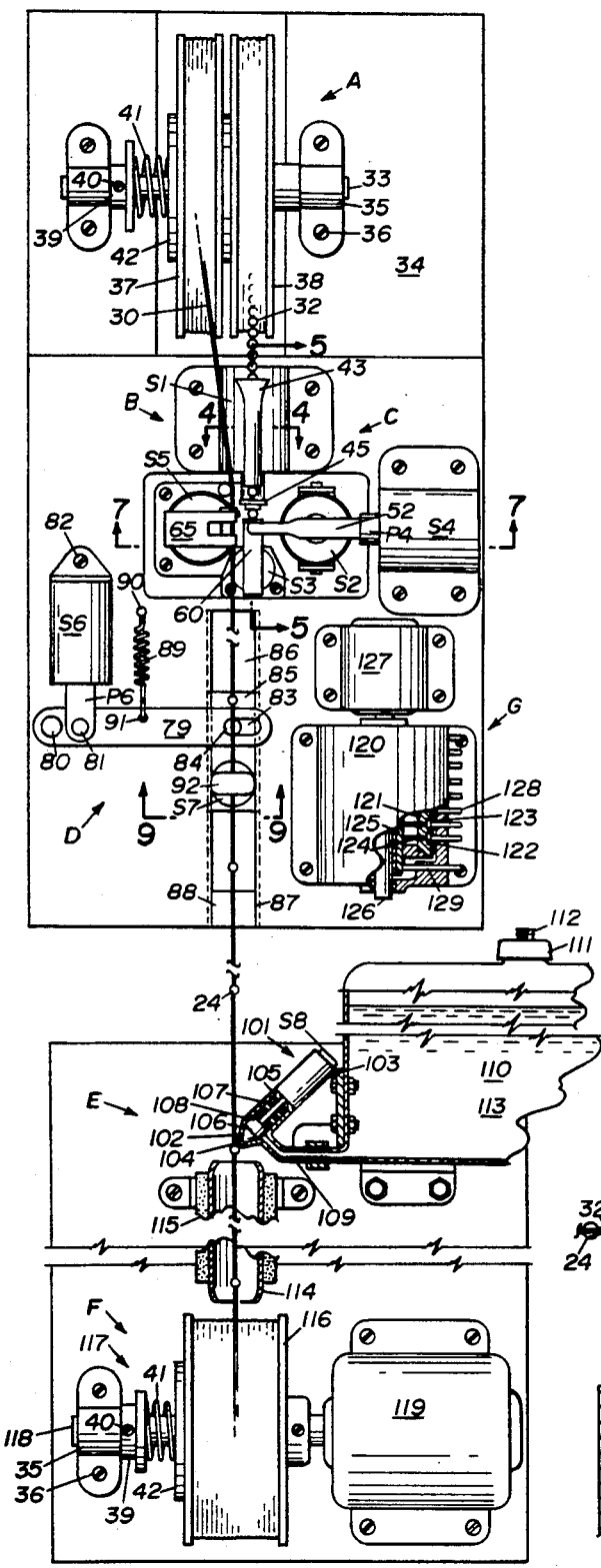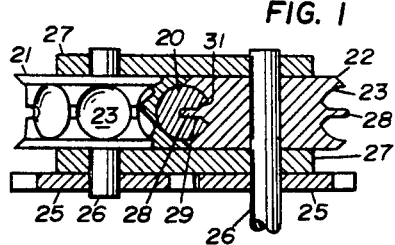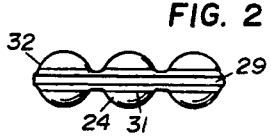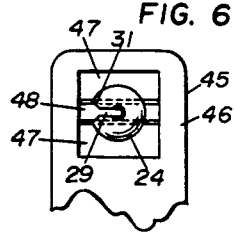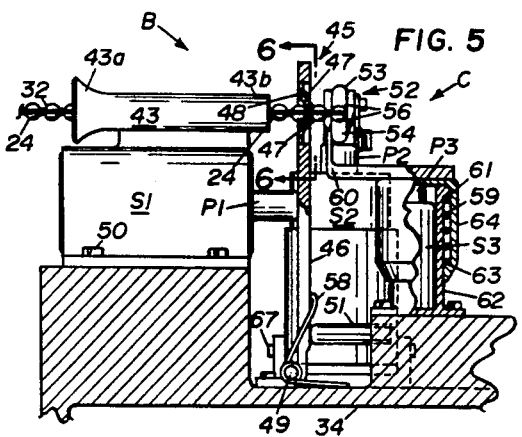

APPARATUS FOR MAKING BEADED DENTAL FLOSS OR THE LIKE

BACKGROUND OF THE INVENTION

1. Field of the Invention

This invention relates to automated methods and apparatus for making beaded dental floss, wherein the beads must be firmly fixed to the floss and located thereon with precision.

2. Description of the Prior Art

Beaded or knotted dental floss is known in the art. U.S. Pat. No. 3,631,869 "Dental Floss Holder" to R. J. Espinosa states (column 2, line 31) "The nubs 1 (on the floss) could constitute drops of hardened material applied in liquid form to a straight, smooth floss. Alternatively, the nubs 1 could comprise pronounced crimps which have been mechanically imparted to normally straight floss fiber or they could even comprise clips applied to the floss mechanically." U.S. Pat. No. 3,974,842 "Disposable Flosser" to I. S. Chodorow states (column 6, line 30) "... beads ... knots, loops or other enlargements of the floss itself.... Beads may be fastened onto the floss by mechanical crimping, or cementing, or any feasible method. A simpler technique would be to simply place a drop of cement or appropriate solvent at 32 where the floss extends ... or a bead or knot at 32." U.S. Pat. No. 1,815,408 "Dental Floss Holder" to J. K. Jordan refers to "knots" on the dental floss. U.S. Pat. Nos. 4,753,254 and 4,776,357, granted to the present inventors, also mentions beaded dental floss.

However, all of these patents are directed primarily toward floss applicators, treating the beaded floss almost as an incidental accessory. Hence, none of them teaches or claims methods or apparatus for making beaded floss, or cites specific materials from which the beads or enlargements on the floss can be made. Therefore, considerable experimentation and inventing would be required in order to actually manufacture beaded floss on the basis of teachings in the cited patents.

As mentioned above, two of the prior-art patents teach knots in the floss as being equivalent to beads in effectiveness. However, no particular kind of knot is specified, nor is it indicated how such a knot would be tied. In the present inventors' experiments, it was observed that knots are inherently asymmetric, and, hence, somewhat more conducive to tangling the floss that is the case with small, symmetrical beads. Also, it is not disclosed how the crimps, as mentioned in the Espinosa patent, would work. It would seem that crimps would simply straighten out when the floss is placed under tension. Also, his hardened material that can be applied to the floss in liquid form leaves many questions, such as: What materials would be used with what kind of floss that would provide the required strength of adhesion? What liquid material would form a bead, rather than simply wick into the floss? How would one form a symmetrical bead on the floss with liquid material?

The "mechanical crimping" of beads, cited in the Chodorow patent, seems to imply metallic beads. This would suggest the possibility of cutting the floss accidentally in the process of such crimping. Similarly, the cementing of beads to the floss, cited in the Chodorow patent, would require experimentation to discover an appropriate cement and bead material that would serve the required purpose, and means for positioning the beads on the floss.

SUMMARY OF THE INVENTION

An object of the present invention, therefore, is to overcome these information deficiencies in the prior art by providing a method and apparatus for making beaded dental floss. Beaded dental floss is useful in conjunction with dental-floss applicators, such as those described in U.S. Pat. Nos. 4,753,254 and 4,776,357, as well as in others cited above.

Another object of the invention is to provide a method for making beaded dental floss easily and inexpensively.

Another object of the invention is to provide an automated method for making beaded dental floss that can produce precision placement of the beads on the floss.

These and other objects and advantages of the invention will become more readily apparent as the following, detailed description is read with reference to the accompanying drawings. The same numbers are used to designate the same parts throughout the drawings.

BRIEF DESCRIPTION OF THE DRAWINGS

In the drawings:

FIG. 1 is a greatly-enlarged edge view of a pair of mold wheels that form beads on an cylindrical, plastic filament (such as an extrusion from a die), some parts are shown in section;

FIG. 2 is a side view of the filament segment after having been passed between the mold wheels of FIG. 1;

FIG. 3 is a plan view of the apparatus for making beaded dental floss (about 50 percent larger than actual size), some parts being broken away and sectioned to show detail;

FIG. 4 is an enlarged cross section of the guide, taken on Line 4—4 of FIG. 3;

FIG. 5 is a sectional view taken on Line 5—5 of FIG. 3 to show how beads are fed into the bead clamp;

FIG. 6 is a view taken on Line 6—6 of FIG. 5 to show a frontal view of the feed clamp;

DESCRIPTION OF THE PREFERRED EMBODIMENTS

Figure 7:
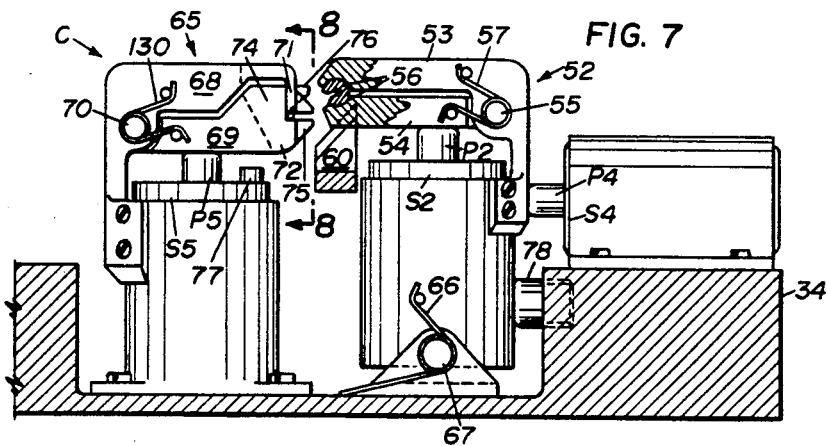
FIG. 7 is a sectional view taken on Line 7—7 of FIG. 3, the solenoids being shown in full, side view and the bead clamp being shown in section for better detail.

FIG. 1 shows a cross section of a cylindrical filament 20 of preferably a thermoplastic material, such as nylon. For the purpose cited above, it is preferably about 0.04 inch in diameter. It can be made by extrusion through any well-known type of die (not shown) commonly used for such purposes. The filament 20, while still in a somewhat plastic state, is passed between an opposing pair of mold wheels 21 and 22. The edges of these wheels have matching, hemispherical cavities 23 that form a bead stock comprising connected, spherical shapes or beads 24 on the filament 20, without interrupting the continuity thereof (FIG. 2). Each of these beads 24 is preferably about 0.045 inch in diameter. Two meshing spur gears 25, one fixed to each of the wheels 21 and 22, insure that the hemispherical cavities 23 are always in precise register with one another. The wheels 21 and 22 are held in the appropriate positions relative to one another by a shaft 26 that extends through the center of each wheel. Each end of each shaft 26 is journaled in holes in a pair of yokes 27, or other support means. One of the wheels is rotated by conventional means, not shown (such as a synchronous, electric motor), attachable to the right-hand shaft 26 as shown in FIG. 1.

The wheel 22 also includes an outwardly-extending flange 28 that bisects the hemispherical cavities 23. The flange 28 forms a longitudinal slit 29 in the beads 24. As shown in FIG. 1, this slit 29 extends into each bead 24 slightly past its center, for symmetrical positioning of the bead on the dental floss 30 (FIG. 3). Also, the outer portion of the slit 29 is flared at 31 to facilitate insertion of the floss. The resulting form of the filament 20 (FIG. 2), is a continuous strand or series 32 of connected beads 24, each containing the slit 29. When the beaded filament 32 is solidified, it is stored on spools or reels.

Alternatively, the filament 20 may be already solidified before being shaped into a beaded form—the mold wheels 21 and 22 being heated (by a conventional means not shown) to a temperature that enables them to form the plastic filament into the beaded configuration.

The apparatus for using the beaded filament 32, described above, to make beaded dental floss is shown in top or plan view in FIG. 3. As shown, the supply unit A has a fixed shaft 33 mounted to a support member or chassis 34 by bearings 35 and screws 36. The shaft 33 holds two storage reels that rotate freely on it—the floss reel 37 and the beaded-filament reel 38. A collar 39, fixed to the shaft 33 by a set screw 40, provides a stationary support for a compression spring 41 that bears against a sliding disk 42 to provide a brake on the reels 37 and 38, as a part of the apparatus that keeps the floss under tension.

The beaded filament 32 is introduced into the loading unit B via a tube 43, having a flared loading end 43a to facilitate loading of the filament therein, and an exit end 43b positioned adjacent a bead clamp (yet to be described). A guide means 44 in the form of a thin, inwardly-extending, radially-oriented flange is fixed to the inside of the tube 43. It fits into the slit 29 of the filament 32 (FIG. 4) to maintain the beads 24 in proper orientation for operation of subsequent mechanisms (FIG. 3).

The loading unit B is loaded when two beads 24 of the beaded filament 32 have been passed through the loading clamp 45 (FIGS. 3 and 5). This clamp 45 has a plate 46 that holds two opposing, leaf springs 47, one above the other, across an opening 48 therein. These leaf springs 47 are both curved forwardly and are of such a length that they can push beads in the direction of their curvatures, but slide over the beads when moving in the opposite direction (if the filament 32 is held in a fixed position). The plate 46 is mounted to the chassis 34 by via a hinge 49.

A first (bead-stock) solenoid S1, mounted to the chassis 34 by screws 50, bears against the plate 46 with its plunger P1 so that the plate is moved away from the solenoid S1 when it is energized. This movement of the plate 46 is limited to approximately the diameter of one bead 24 by a threaded stop 51 that screws into the chassis 34; and its purpose is to deliver the end bead 24 of the beaded filament 32 to the bead-pressing unit C (FIGS. 3, 5 and 7).

The bead clamp 52 has an L-shaped member 53 and a straight member 54 pivoted thereto at 55. The outer-end portions of the members 53 and 54 are equipped with opposing, spherical surfaces or jaws 56 for grasping a bead 24. A torsion spring 57, fastened to the pivot 55 and bearing against pins on the clamp members 53 and 54, bias these members apart to insure release of the bead 24 and return of the plunger P2 to it original position when the (bead-clamp) solenoid S2 is de-energized. The L-shaped member 53 is fixed to the mounting case of a vertically-positioned, second solenoid S2. The mounting case of this solenoid is pivotally mounted at 67 by two pins extending from its base and journaled in holes in a bracket fixed to the chassis 34, so that it can swing at right angles to the motion of the first solenoid S1, moving the bead clamp 52 toward a span of floss being held by a clamp to be described later. The bead clamp 52 can be operatively mounted to the chassis 34 by other means that will permit this motion, such as a sliding, tongue-and-groove joint, etc. The bead clamp 52 firmly grasps a bead 24 delivered to it by the spring clamp 44, when the second solenoid S2 is energized and its plunger P2 forces the jaws 56 together. When this happens, the first solenoid S1 is de-energized and a second torsion spring 58, attached to the pivot 49 on the loading-clamp plate 46 and bearing against this plate and the chassis 34, returns the loading clamp 45 to its original position. In doing so, the two opposing leaf springs 47 of the loading clamp 45 slide back over one bead of the beaded filament 32, preparing the next bead to be fed into the bead clamp 52.

As best shown in FIG. 5, a third solenoid S3 is mounted, via a mounting case, in a fixed, vertical position to the chassis 34. When the second solenoid S2 is energized, causing the bead 24 in the bead clamp 52 to be firmly grasped thereby, the third (knife-operating) solenoid S3 is energized. A knife 60, actuated by the plunger P3, then severs the connection between the bead 24 being grasped by the bead clamp 52 and the adjacent bead 24 of the beaded filament 32. The plunger P3 bears against the closed end of a cylindrical mounting sleeve 64 to which the knife 60 is fixed, and which slides longitudinally on the solenoid case 62. The closed end of the sleeve 64 may be any obstruction, fixed to the sleeve, against which the plunger P3 can bear to move the sleeve. When this cutting action is completed, the third solenoid S3 is de-energized, and the knife 60 is forced back to its original position by a compression spring 59. This spring 59 is trapped between a shoulder 61 on the solenoid mounting case 62 and one 63 on the inside of the sleeve 64.

A fourth (bead-pressing) solenoid S4 is mounted, via a mounting case, in a position parallel to the chassis 34 by screws so that its plunger P4 can move the solenoid S2 (FIG. 7). When the bead 24 being grasped by the bead clamp 52 is severed from its adjacent bead 24 by the knife 60, the fourth solenoid S4 is energized. This moves the second solenoid S2 and presses the grasped bead 24 firmly onto a strand of dental floss 30, which is being held in a horizontal position at right angles to the motion of the bead clamp 52 by the first floss clamp 65 (FIG. 7). A torsion spring 66, fastened to the pivot 67 and bearing against the chassis 34 and a pin on the mounting case of the solenoid S2, returns this solenoid and the plunger P4 to their original positions, when the solenoid S4 is de-energized.

Figure 8:
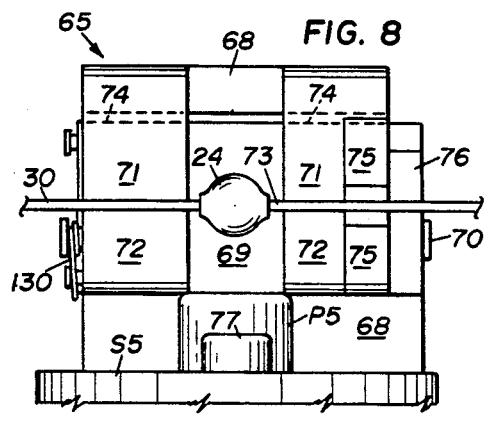
FIG. 8 is a greatly-enlarged frontal view of the floss clamp taken on Line 8—8 of FIG. 7, showing a bead pressed onto the floss.

The first floss clamp 65 is similar in construction to the bead clamp 52, having an L-shaped member 68 that is mounted to the housing of a fifth (floss-clamp) solenoid S5 and a substantially-straight member 69 pivoted thereto at 70. Both members 68 and 69 are bifurcated to provide a pair of jaws 71 and 72 to hold the ends of a span of floss 73 that is grasped thereby (FIGS. 7 and 8). As shown in FIG. 7, each of the lower jaws 72 has a raised portion 74 that acts as a stop means for preventing the floss 30 from moving with the motion of the bead 24 when the bead is being pressed onto it. The forward portions of the upper jaws 71 are curved downwardly to slide over these raised portions 74 of the lower jaws 72. As shown in FIG. 8, each of the jaws 71 and 72 has a forward projection 75 on the right-hand side of its right-hand bifurcation. These projections 75 serve as guides for retention of the floss 30 when the jaws 71 and 72 are opened after a bead has been pressed onto the floss span 73. When these jaws are opened, a diagonal projection 76 on the right-hand side of the lower jaw 72 moves the floss 30 forward, so that it clears the jaws 71 and 72 but is still retained in vertical directions by the projections 75. The purpose of this is to allow the pressed on bead 24 to clear the left-hand jaws 71 and 72 when the floss 30 is moved longitudinally for placement of the next bead.

The solenoid S5 is mounted, via a mounting case, perpendicular to the chassis 34, and the L-shaped member 68 is mounted to its case. The floss 30 is firmly grasped by the jaws 71 and 72 when the solenoid S5 is energized so that its plunger P5 forces the lower jaws 72 against the upper jaws 71. At that time, the solenoid S4 is energized to move the bead clamp 52 toward the span of floss 73 that lies between the bifurcated jaws of the floss clamp 65. It is on this span 73 that the bead 24, being held in the bead clamp 52, is press-fitted. Hence, this span of floss 73 is only slightly longer than one bead diameter, to facilitate precise placement of a bead 24 thereon. When the bead 24 has been thus mechanically fixed to the floss, the second and fourth solenoids (S2 and S4) are simultaneously de-energized. The fifth solenoid S5 remains energized for a very short time longer to facilitate disengagement of the bead clamp 52 from the pressed-on bead 24. Downward movement of the lower jaws 72 is insured by a torsion spring 130 fastened to the pivot 70 and bearing against pins in the members 68 and 69 to bias them apart. This movement is restricted by a small stop 77 that prevents the raised portions 74 from clearing the upper jaws 71. When the fourth solenoid S4 is de-energized, the torsion spring 66 moves it and the bead clamp 52 back into their original positions. Precision of this repositioning is insured by a threaded stop 78 that is screwed into the chassis 34 and bears against the mounting case of the solenoid S2.

Figure 9:
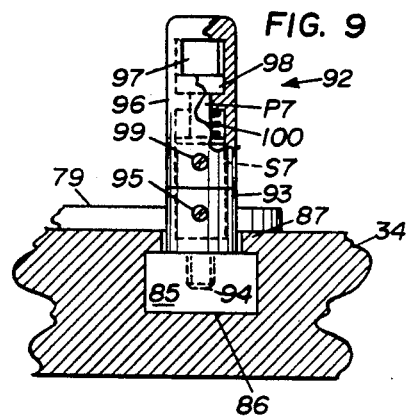
FIG. 9 is a frontal view taken on Line 9—9 of FIG. 3, showing the second floss clamp, with some parts broken away to show detail.

When the fifth solenoid S5 is de-energized, allowing the floss clamp 65 to open, the sixth (floss-measuring) solenoid S6 (in the floss-measuring unit D) is energized to operate the floss-measuring arm 79 (FIG. 3). This arm is pivotally mounted at 80 to the chassis 34. The solenoid plunger P6 is pivotally fastened to the arm 79 at 81, so that the arm 79 can swing through a relatively large arc. To permit this arcuate motion, the solenoid S6 is pivotally mounted to the chassis 34 at 82. Heretofore, all movements of the solenoids have been very small (of the order of about one to three bead diameters). However, the arm 79 must measure a length of floss 30 of approximately one-and-one-sixteenths inch long (the preferred distance between beads thereon). The free end of the floss-measuring arm 79 has a longitudinal slot 83 to receive a vertical pin 84 fixed to the floss-moving carriage 85. This carriage is a rectangular block seated in an elongated, rectangular cavity 86 in the chassis 34. As shown in FIG. 9, the carriage block 85 is retained by two short, longitudinal flanges 87 at the upper surface of the cavity 86, and by the stop block 88 that is press fitted into the open end of the cavity 86. The carriage block 85 moves back and forth in the cavity 86 in response to movement of the floss-measuring arm 79, the length of this travel being exactly equal to the desired distance between beads 24 on the floss 30. When the solenoid S6 is de-energized, the arm 79 and the carriage block 85 are returned to their starting positions by a tension spring 89 that is anchored at one end to the chassis 34 by a pin 90. At its other end it is hooked into a hole 91 in the floss-measuring arm 79.

A second floss clamp 92 (FIGS. 8 and 9) is fixed to the upper surface of the carriage block 85 via a mounting cup 93 for the seventh (floss-moving) solenoid S7. The mounting cup 93 has a threaded stud 94 that is screwed into a threaded hole in the carriage block 85. The solenoid S7 is retained in the cup 93 by a set screw 95. The upper portion of the solenoid S7 is covered by a cap 96, secured thereto by a set screw 99, which forms the second (floss-moving) floss clamp 92. This clamp 92 is formed by a flattened portion of the cap 96 that contains a square aperture 97. A bar 98, fastened to the plunger P7 of the solenoid S7 moves in this flattened portion to close the aperture 97, securely clamping the floss 30 that passes therethrough when the solenoid S7 is energized.

When a bead 24 has been pressed onto the floss 30 and solenoid S5 has been de-energized, both solenoids S6 and S7 are energized to move a measured segment of floss 30 longitudinally so that the floss in the first floss clamp 65 is in the proper position for placement of another bead 24 thereon. The second floss clamp 92 is positioned to grasp the floss 30 between beads 24, and the floss, under tension, is positioned to pass through the center of the open aperture 97 so that each bead can pass therethrough without touching the edges of the aperture 97. The cap 93 is secured to the solenoid S7 by a set screw 99. The bar 98 and the plunger P7 are returned to their normal positions by an internal compression spring 100, when the solenoid S7 is de-energized.

The pressed on bead 24 next goes to the gluing-and-drying unit E. A glue dispenser 101 is positioned so that the action of the floss-measuring arm automatically places each bead, in turn, adjacent a nozzle 102 thereon. The glue dispenser 101 has a cylindrical housing, or other hollow body, 103 that has the conic nozzle 102 with a tiny orifice 104 in its tip. The opposite end of the housing 103 holds the eighth (gluing) solenoid S8, the plunger P8 of which extends through a hole in a sealed partition 105 and is attached to a conic piston 106. This piston 106 fits the conic form of the inside of the nozzle 102 and is normally forced against it by a compression spring 107 that is confined between the partition 105 and the piston 106, thus maintaining the orifice 104 in a normally-closed position. A short, cylindrical portion 108 of the piston 106 also maintains the opening of a tube 109 closed. This tube 109 leads to a pressurized container 110 of glue. The glue container 110 is equipped with a common, threaded cap 111 with a conventional, pressurizing fitting 112 containing a check valve (not shown) whereby the container can be pressurized to about two atmospheres of air pressure.

When a bead 24 is moved to its position adjacent the glue dispenser nozzle, the solenoid S8 is energized, briefly pulling the piston away from the orifice 104 and the opening of the tube 109. This permits the pressurized glue 113 to flow through the tube 109 and into the interior of the nozzle 102. When the solenoid S8 is de-energized, the spring 107 forcibly expels the appropriate quantity of glue onto the juncture of the bead 24 and floss 30. The bead then passes through a long tube 114 that is heated by conventional electric means, represented at 115, to about 200 degrees F. This sets and dries the glue sufficiently for it to be stored on a take-up reel 116.

In order to handle the floss 30 with precision, it must be held under at least about 2.5 ounces of tension. This has been found to be sufficient to remove kinks in nylon floss sold commercially under the label "extra fine," to insure that it is perfectly straight. Heavier types of floss may require somewhat more tension for this purpose. Such tension is achieved by pressure exerted by the brake disk 42 (described above) on the floss-supply reel 37, together with the action of the take-up reel 116 and its electric motor 119. To achieve this tension, the take-up unit F (FIG. 3) has a take-up reel 116 equipped with a braking structure 117 identical to that described for the supply reel 37. The take-up reel, like the supply reel, is allowed to move freely on the shaft 118 that is rotated by an electric motor 119.

Although many bonding agents are suitable for the purpose of gluing the beads 24 to the floss 30, a cyanoacrylate-containing adhesive sold under the trade name Krazy Glue by Krazy Glue, Inc. of Itasca, Ill. has been found to work very well.

Figure 10:
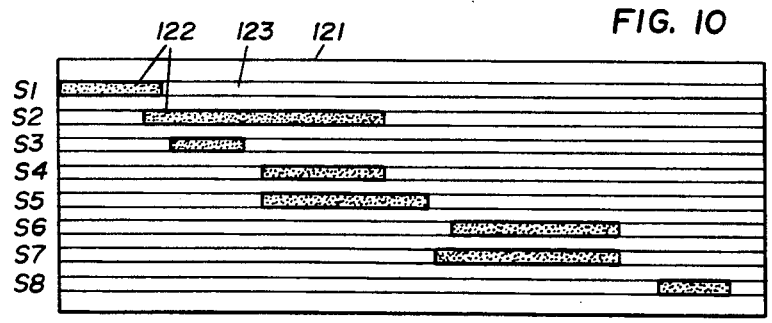
FIG. 10 is a flat view of the surface of the rotating drum of the timer, to show the approximate, relative times during which individual solenoids are in operation during the installation of each bead on the floss.
Figure 11:
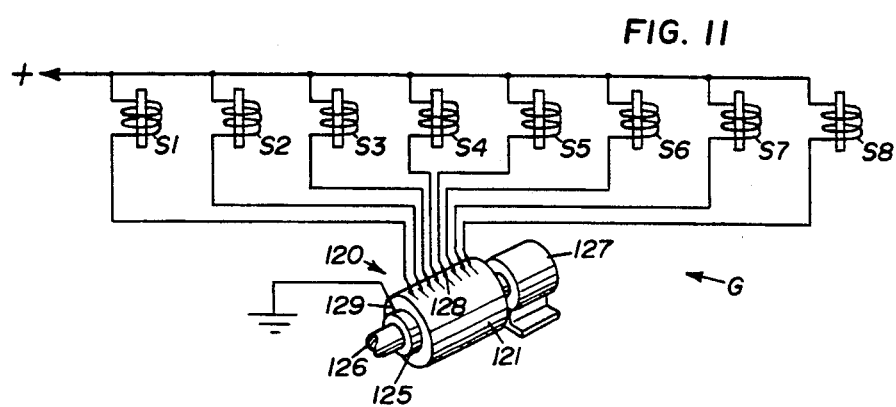
FIG. 11 is a simplified, schematic wiring diagram of the electrical system of the apparatus.

A roughly-sequential operation of the eight solenoids described above is necessary for the emplacement and bonding of any one bead to the floss. In this process, certain functions must be completed before others can be initiated. For example, the function of solenoid S1 in placing a bead between the jaws of the clamp 52 must be completed before the solenoid S2 is energized to close those jaws. Similarly, S2 must be energized to close the clamp 52 and S1 must be de-energized to load the next bead 24 into the loading clamp 45 before the solenoid S3 is energized to sever the grasped bead from the remainder of the beaded filament 32. Hence, it is obvious that exact timing of the operations of the solenoids is important. This timing can be accomplished by any of a number of well-known means. Such means include: computer software, electronic timers, and mechanical timers. Since there are only eight circuits (one for each solenoid) to be opened and closed in a sequential pattern, a simple, electromechanical timer 120 is effective (FIGS. 3, 10, and 11). A drum 121, made of an electrically-nonconductive material, such as virtually any plastic, holds elongated conductors 122, oriented circumferentially, in grooves 123 in its surface. These conductors 122 function as switches to turn the solenoids on and off. Each conductor 122 is connected by a wire 124 (FIG. 3) to a common, annular conductor 125 that is insulated from the shaft 126 about which it is rotated by a motor 127 (FIG. 11). All of the solenoids are preferably connected (by conductors having the same polarity) to this annular conductor 125 via brush connectors 128. The annular connector, in turn, is connected into the circuit by a brush connector 129 that remains in contact with the annular connector as it is rotated. The lengths of the conductors 122 and the rotational speed of the drum 121 are optimized to give each solenoid time to perform its assigned function.

The desired time sequence for operation of the solenoids is illustrated in FIG. 10, which is a flat view of the surface of the drum 121. The elongated, stippled rectangles represent the conductors 122.

A simplified, schematic wiring diagram is shown as FIG. 11. The solenoids, S1 through S8, are essentially connected in parallel configuration to a DC source of current; and are switched on and off as the drum 121 rotates.

The foregoing description of the apparatus and method of the invention has been related with regard to very specific examples. However, it should be noted that there are alternative means of performing each function of the invention, which is defined by the following claims.

The invention claimed is:

1. Apparatus, using bead stock comprising a continuous strand of tandemly-connected beads with a slit in one side thereof, for fixing a bead on dental floss, comprising:
   guide means, using the slit in the bead stock as an index for axial orientation thereof;
   means for feeding the bead stock through the guide means;
   a bead clamp means for grasping the end bead of the bead stock and holding it as oriented by said guide means;
   means for firmly holding the ends of a span of floss;
   means for severing said held bead from said bead stock; and
   means for pressing said bead onto said span of floss, so that the floss is pressed into the slit in the bead.

2. The apparatus of claim 1 wherein said clamp for holding a single bead of bead stock comprises:
   a pair of opposed jaws operatively connected together so that at least one of the jaws can be moved toward the other for grasping said bead; and
   means for moving at least one of said jaws toward the other.

3. The apparatus of claim 2 wherein said means for moving one of said jaws toward the other comprises bead-clamp solenoid having a plunger and fastened to said clamp so that said plunger forces one of said jaws toward the other when the solenoid is energized, to grasp said held bead.

4. The apparatus of claim 1, wherein said means for holding the span of floss comprises:
   a first floss clamp having a pair of opposing, bifurcated jaws, operatively connected together so that at least one of said jaws can be moved toward the other for grasping said floss; and
   means for moving at least one of said jaws toward the other.

5. The apparatus of claim 4 wherein said means for moving at least one of said jaws toward the other comprises:
   a floss-clamp solenoid having a plunger and fastened to said clamp so that the plunger forces one of said jaws toward the other when the solenoid is energized to grasp the floss and to form a held span thereof between said bifurcated jaws.

6. The apparatus of claim 5 including spring means on the first floss clamp that biases the jaws thereof away from one another, to facilitate release of the floss when said floss-clamp solenoid is de-energized.

7. The apparatus of claim 1 wherein the means for severing said held bead from bead stock comprises:
a knife, the cutting edge of which is normally positioned adjacent the bead stock; and
means for moving said knife to cut the bead stock at the connection between said held bead and the adjacent bead on the bead stock.

8. The apparatus of claim 7 wherein said means for moving the knife comprises a knife operating solenoid having a plunger that can be operatively in contact with said knife, so that the knife moves to cut the filament when the solenoid is energized.

9. The apparatus of claim 8 further including a common support member that operatively supports both said bead clamp and said knife.

10. The apparatus of claim 8 further including a case for mounting said knife-operating solenoid to the support member and a sleeve that fits over said case for sliding motion longitudinally thereon, and wherein said knife is fixed to said sleeve and wherein the sleeve further includes an obstruction fixed thereto against which said plunger can bear to move the sleeve.

11. The apparatus of claim 1 wherein the means for pressing the held bead onto said span of floss comprises:
a support member;
mounting means for movably mounting the bead clamp to the support member;
a bead-pressing solenoid fixed to the support member and having a plunger that operatively bears against the bead clamp to move it toward said span of floss until the floss thereof is pressed into the slit in the bead.

12. The apparatus of claim 11 wherein the mounting means for movably mounting the bead clamp to the support member comprises: a mounting case for the bead-clamp solenoid, having two diametrically opposite pins extending outwardly from its base portion; and a bracket fixed to said support member, having holes in which the pins are journaled for pivotal motion of the case, said bead clamp being attached to the case so that it moves therewith.

13. The apparatus of claim 1 wherein said guide means comprises: a tube for passage therethrough of the filament, slightly larger in diameter than said filament and having a loading end and an exit end; and a thin, radially-oriented flange fixed longitudinally to the inside of the tube, so that it will extend into the slit in said beaded filament to prevent axial rotation thereof, the exit end of the tube being fixed adjacent the bead clamp.

14. The apparatus of claim 13 wherein the loading end of the tube is flared outwardly to facilitate loading of the filament therein.

15. The apparatus of claim 1 further including means for loading an end bead of bead stock into the bead clamp comprising:
a support member;
loading-clamp means movably mounted to said support member and capable of holding an end of bead stock adjacent the bead clamp; and
means for moving the loading-clamp means toward the bead clamp so that the end bead of the bead stock being held thereby will be placed in a position to be grasped by the bead clamp.

16. The apparatus of claim 15 wherein the loading-clamp means comprises:
a plate, pivotally mounted at one end to said support member and having an aperture in the other end portion thereof;
a pair of opposing leaf springs, each fixed at one end to one side of the aperture and extending toward the other, and being curved outwardly from the same face of the plate so that, when bead stock is passed through the aperture and between the leaf springs, the curved end portions of the springs can act to push a bead of the bead stock in one direction, but, when an end bead thereof is grasped by the bead clamp, the leaf springs can slide back over an adjacent bead when the loading-clamp means moves in the other direction; and
means for moving the loading-clamp toward the bead clamp.

17. The apparatus of claim 15 wherein the means for moving the loading clamp toward the bead clamp comprises:
a bead-stock solenoid mounted to the support member and having a plunger that can bear against said plate to move it toward the bead clamp for loading an end bead of the filament therein; and further includes spring means biasing said plate toward the bead-stock solenoid, so that, after having been moved by the solenoid, it is returned to its original position when the solenoid is de-energized.

18. Apparatus, using bead stock comprising a continuous strand of tandemly-connected beads with a slit in one side thereof, for fixing beads onto dental floss at spaced intervals comprising:
guide means, using the slit in the bead stock as an index for axial orientation thereof;
means for feeding the bead stock through the guide means;
a clamp means for grasping the end bead of the bead stock and holding it as oriented by said guide means;
means for firmly holding the ends of a span of floss;
means for severing said held bead from the bead stock;
means for pressing said held bead onto said span of floss, so that the floss is pressed into the slit in the bead;
means for removing the held bead from said clamp; and
means for moving a pressed-on bead longitudinally for a distance which is the desired spacing between beads on the floss.

19. The apparatus of claim 18 wherein said means for moving the floss comprises:
a support member;
a lever arm pivoted at one end to the support member;
a second floss clamp, operatively attached to the other end of the lever arm for grasping said floss on demand;
means for causing the second floss clamp to grasp the floss;
means for causing the second floss clamp to release the floss;
means for moving said lever arm about its attachment to said support member;
means for limiting the distance through which said second floss clamp can move to the desired distance between beads on the floss; and
means for returning the lever arm to its original position after it has been rotated to move the second floss clamp.

20. The apparatus of claim 19 wherein the second floss clamp is mounted to the support member for linear sliding motion thereon parallel to the floss, and wherein the attachment of said second floss clamp to said lever arm comprises a pin-in-slot arrangement wherein a pin fixed to one of said members rides in an elongated slot in the other for converting the arcuate motion of the end portion of said arm to linear motion of said second floss clamp relative to the support member.

21. The apparatus of claim 20 further including a rectangular carriage block seated in an elongated, rectangular cavity in the support member, the length of the cavity being equal to that of the carriage block plus that of the desired distance between beads on the floss, and wherein both a pin that fits into a slot in the end portion of said lever arm and said second floss clamp are fixed to the carriage block.

22. The apparatus of claim 19 wherein the means for moving the lever arm comprises a sixth solenoid having a plunger pivotally attached to said lever arm, the other end of the solenoid being pivotally mounted to the support member.

23. The apparatus of claim 19 wherein said means for returning the lever arm to its original position after having been moved comprises spring means attached at one end to the lever arm and at the other to the support member.

24. The apparatus of claim 19 wherein the second floss clamp comprises: floss-moving solenoid having a plunger; and a member fixed to the solenoid and configured so that a portion thereof extends into the line of motion of the plunger so that the plunger can operatively bear against said member, whereby floss can be clamped between the plunger and said member.

25. The apparatus of claim 18 further including means for sealing the pressed-on bead with glue.

26. The apparatus of claim 25 wherein said means for sealing the pressed-on bead to said dental floss comprises:
a pressurized container for holding liquid glue;
means for pressurizing said container;
a small, hollow body defining a cylindrical chamber that tapers at one end to form a hollow cone having a tiny orifice in the end thereof;
a piston that fits inside said chamber for longitudinal motion therein, the piston having a conic end portion that fits the conic portion of said chamber, the piston having a central shaft that extends through a hole in the end of the hollow body opposite the orifice, and said hollow body having an opening that communicates with the interior of said pressurized container, this opening being located so that it is normally closed when the piston is seated in the conic portion of the hollow body, but is opened when the piston is pulled back from the orifice, allowing glue to fill the conic portion of said hollow body; and
means for moving said piston within the hollow body.

27. The apparatus of claim 26 wherein the means for moving the piston within the hollow body comprises:
an gluing solenoid having a plunger attached to the central shaft of the piston; and
spring means operatively attached to said piston, so that the gluing solenoid, when energized, moves the piston in one direction relative to the orifice and the spring means moves it in the opposite direction, so that one of these two elements moves the piston away from the orifice to allow glue to enter the conic chamber and the other moves the piston back toward the orifice to expel the glue therethrough.

28. The apparatus of claim 18 further including means for maintaining said floss under tension sufficient to remove any kinks therein, so that measurements between beads thereon can be accurately made.

29. The apparatus of claim 28 wherein said tensioning means comprises:
a support member;
a floss-supply reel pivotally attached to said support means;
a brake on said floss-supply reel that prevents rotation of said reel unless tensile force is exerted thereon that is greater than the tension to be maintained on the floss;
a floss take-up reel pivotally attached to the support member;
a motor having a central shaft which comprises a portion of the pivotal attachment of the floss take-up reel to said support means, and on which the floss take-up reel rotates; and
a brake that bears against the take-up reel, so that it rotates with the motor shaft until the tensile force on the floss being wound on said take-up reel reaches the desired tension.

30. The apparatus of claim 29 wherein the brake on the floss-supply reel is substantially the same as that on the take-up reel and comprises:
a disk concentric with its respective reel and bearing against it; and
spring means that bears at one end against said support member and at the other against said disk to force it against the reel.

31. The apparatus of claim 18 further including a timing means for regulating the time periods during which each of the eight solenoids is energized and de-energized relative to the others.

32. The apparatus of claim 31 wherein said timing means comprises:
a rotating drum of electrically-nonconductive material;
electrical conductors in the surface of said cylindrical drum, the conductors being arranged in juxtaposition in said surface and having circumferential lengths proportional to the periods of operation of the solenoids;
an annular conductor concentric with the drum and connected to each of said surface conductors; and
brush connectors for connecting said annular conductor and said drum-surface conductors to the solenoids.

* * * * *